(12) United States Patent
Meeusen et al.

(10) Patent No.: US 11,889,670 B2
(45) Date of Patent: Jan. 30, 2024

(54) ELECTROMAGNETIC INTERFERENCE SHIELDING OF MEMS MICROPHONE VIA PRINTED CIRCUIT BOARD

(71) Applicant: Cochlear Limited, Macquarie University (AU)

(72) Inventors: Tom Meeusen, Macquarie University (AU); Koen Erik Van den Heuvel, Macquarie University (AU); Jan Vermeiren, Macquarie University (AU); Stijn Eeckhoudt, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 286 days.

(21) Appl. No.: 17/293,447

(22) PCT Filed: Apr. 1, 2020

(86) PCT No.: PCT/IB2020/053103
§ 371 (c)(1),
(2) Date: May 12, 2021

(87) PCT Pub. No.: WO2020/208481
PCT Pub. Date: Oct. 15, 2020

(65) Prior Publication Data
US 2021/0410340 A1    Dec. 30, 2021

Related U.S. Application Data

(60) Provisional application No. 62/833,354, filed on Apr. 12, 2019.

(51) Int. Cl.
*H04R 25/00*    (2006.01)
*H05K 9/00*    (2006.01)
(Continued)

(52) U.S. Cl.
CPC ....... *H05K 9/0024* (2013.01); *A61N 1/36038* (2017.08); *H04R 25/606* (2013.01);
(Continued)

(58) Field of Classification Search
CPC .... H04R 19/04; H04R 1/04; H04R 2201/003; H04R 9/06; H04R 31/006; H04R 1/028
See application file for complete search history.

(56) References Cited

U.S. PATENT DOCUMENTS 8,536,663 B1    9/2013    Kuo et al.
9,078,063 B2    7/2015    Loeppert et al.
(Continued)

FOREIGN PATENT DOCUMENTS

EP    2757808 A2    7/2014
EP    2757808 A3    7/2016
(Continued)

OTHER PUBLICATIONS

Cirrus Logic, "General Design Considerations for MEMS Microphones," WAN_0284 (2014).
(Continued)

*Primary Examiner* — Amir H Etesam
(74) *Attorney, Agent, or Firm* — Knobbe, Martens, Olson & Bear, LLP

(57) ABSTRACT

An assembly is provided which includes a package and a printed circuit board. The package includes a housing bounding a region and an acoustic sensor within the region. The housing includes a base with a first hole. The sensor is configured to generate signals indicative of sound received by the sensor through the first hole. The printed circuit board is in mechanical communication with the base and includes a second hole aligned with the first hole such that sound received by the second hole propagates through the first hole to the sensor. The printed circuit board further includes an
(Continued)

electrically conductive layer, at least a portion of which extends across the second hole and is configured to allow the sound to propagate through the second hole and to at least partially shield the region containing the sensor from electromagnetic interference.

27 Claims, 6 Drawing Sheets

(51) Int. Cl.
*A61N 1/36* (2006.01)
*H05K 1/11* (2006.01)

(52) U.S. Cl.
CPC ........... *H04R 25/609* (2019.05); *H04R 25/65* (2013.01); *H05K 1/111* (2013.01); *H05K 9/0064* (2013.01); *H05K 9/0067* (2013.01); *H04R 2201/003* (2013.01); *H04R 2225/67* (2013.01); *H05K 2201/10151* (2013.01)

(56) References Cited

U.S. PATENT DOCUMENTS

| 9,794,661 | B2 | 10/2017 | Watson et al. |
|---|---|---|---|
| 2007/0013052 | A1 | 1/2007 | Zhe et al. |
| 2013/0343590 | A1* | 12/2013 | Nakagawa .............. H04R 1/04 381/361 |
| 2014/0044297 | A1 | 2/2014 | Loeppert et al. |
| 2014/0103464 | A1 | 4/2014 | Bolognia et al. |
| 2014/0205127 | A1 | 7/2014 | Khenin et al. |
| 2018/0249242 | A1 | 8/2018 | Minervini |

FOREIGN PATENT DOCUMENTS

| GB | 2561403 A | 10/2018 |
|---|---|---|
| GB | 2561925 A | 10/2018 |
| WO | WO 2017/027242 A1 | 2/2017 |

OTHER PUBLICATIONS

Feiertag et al., "Determining the acoustic resistance of small sound holes for MEMS microphones," Procedia Engineering, vol. 25, pp. 1509-1512 (2011).

Fenical, "Rule-of-Thumb for Calculating Aperture Size," Laird Tech Notes, #154 (2003).

International Search Report and Written Opinion for PCT/IB2020/053103 dated Jul. 8, 2020 in 14 pgs.

Sonion, Microphone O8AC03 Data Sheet (2017).

Extended European Search Report of Application EP20787579.0, dated Nov. 15, 2022 in 7 pages.

* cited by examiner

US 11,889,670 B2

ELECTROMAGNETIC INTERFERENCE SHIELDING OF MEMS MICROPHONE VIA PRINTED CIRCUIT BOARD

BACKGROUND

Field

The present application relates generally to auditory prostheses, and more specifically to microphone assemblies for auditory prostheses.

Description of the Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers, or other functional mechanical or electrical component that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect disclosed herein, an assembly is provided which comprises a package and a printed circuit board. The package comprises a housing bounding a region and an acoustic sensor within the region. The housing comprises a base with a first hole. The sensor is configured to generate signals indicative of sound received by the sensor through the first hole. The printed circuit board is in mechanical communication with the base. The printed circuit board comprises a second hole aligned with the first hole such that sound received by the second hole propagates through the first hole to the sensor. The printed circuit board further comprises an electrically conductive layer. At least a portion of the layer extends across the second hole. The portion is configured to allow the sound to propagate through the second hole and to at least partially shield the region containing the sensor from electromagnetic interference.

In another aspect disclosed herein, a method is provided which comprises providing a microphone package comprising an acoustic port. The package is configured to be surface-mounted onto a printed circuit board and is configured to generate signals indicative of sound received by the acoustic port. The method further comprises providing the printed circuit board. The printed circuit board comprises a hole and an electrically conductive layer extending across the hole. The method further comprises mounting the package onto a surface of the printed circuit board such that sound received by the hole propagates to the acoustic port.

In another aspect disclosed herein, an apparatus is provided which comprises a microphone and a printed circuit board. The microphone comprises a pressure transducer and a planar housing portion. The microphone has a first frequency response to pressure waves. The printed circuit board comprises a first surface in mechanical communication with the planar housing portion and a second surface opposite to the first surface. The printed circuit board further comprises a hole extending from the first surface to the second surface and in fluidic communication with the pressure transducer. The printed circuit board further comprises an electrically conductive mesh within the hole. The hole and the mesh are configured to alter an acoustic impedance of the hole such that the assembly has a second frequency response to pressure waves different from the first frequency response.

BRIEF DESCRIPTION OF THE DRAWINGS

Embodiments are described herein in conjunction with the accompanying drawings, in which.

DETAILED DESCRIPTION

Figure 1:
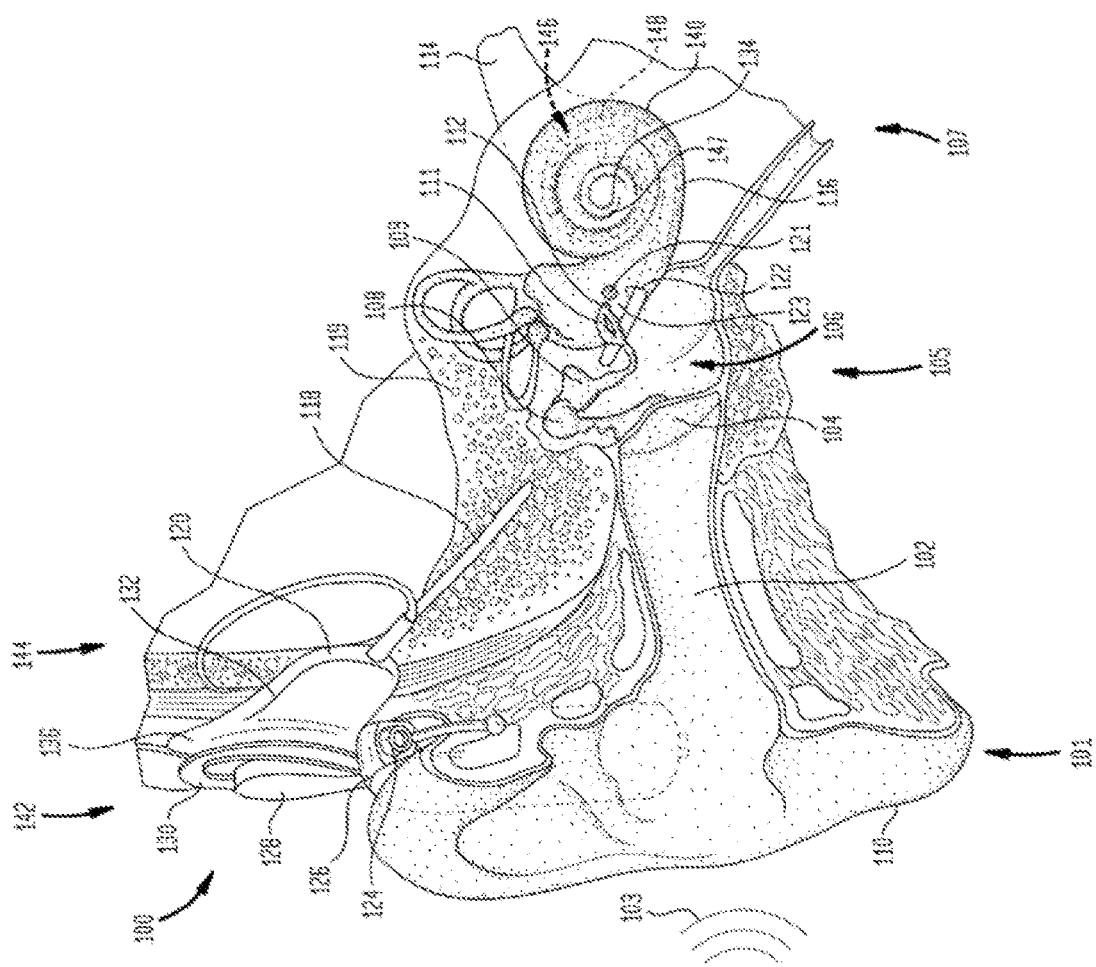
FIG. 1 is a perspective view of an example cochlear implant auditory prosthesis implanted in a recipient in accordance with certain embodiments described herein.

Certain embodiments described herein provide a microphone assembly that includes a bottom port MEMS microphone package mounted onto a printed circuit board (PCB) comprising an electrically conductive mesh extending across the hole in fluidic communication with the acoustic port of the package, the mesh configured to shield (e.g., mitigate; reduce; block; prevent) electromagnetic interference (EMI) and/or electrostatic discharge (ESD) from damaging or otherwise adversely affecting the performance of the package. By having the PCB comprise the mesh, certain embodiments advantageously improve the performance of digital and analog bottom port MEMS microphone packages in external and implanted microphone assemblies. Certain embodiments advantageously decouple the EMI and/or ESD shielding of the hole from the performance attributes of the MEMS microphone package by having the mesh within the PCB, thereby allowing the use of a wider variety of MEMS microphone packages with the selection not being constrained by the shielding provided by the package itself. For example, the mesh can be designed according to a customer's specific EMI and/or ESD shielding requirements by changing the dimensions of the mesh (e.g., hatched polygon pattern, aperture size, thickness, and number of apertures). For another example, the mesh can be designed according to a customer's specific acoustic response requirements by changing the dimensions of the mesh (e.g., hatched polygon pattern, aperture size, thickness, and number of apertures). By having the mesh within the PCB, rather than outside the PCB sandwiched between a gasket and a casing as in some systems, certain embodiments described herein advantageously reduce the overall thickness of the assembly, thereby making the assembly more compatible with implantable configurations.

Some medical devices include an acoustic sensor assembly configured to receive sound, which can be generated externally and/or internally to the recipient, and to generate signals (e.g., electrical signals) in response to the received sound. For example, auditory prostheses that include at least one microphone assembly configured to generate signals indicative of received ambient sound are used to improve the lives of recipients with hearing loss (e.g., which can be due to many different causes and is generally of two types, conductive and/or sensorineural) Conductive hearing loss occurs when the normal mechanical pathways of the outer and/or middle ear being impeded, for example, by damage to the ossicular chain or ear canal. Sensorineural hearing loss occurs when there is damage to the inner ear, or to the nerve pathways from the inner ear to the brain. Such devices include, for example, hearing aids, cochlear implants, bone conduction implants, middle ear implants, and electro-acoustic devices.

Individuals who suffer from conductive hearing loss typically have some form of residual hearing because the hair cells in the cochlea are undamaged. As a result, individuals suffering from conductive hearing loss might receive an auditory prosthesis that generates mechanical motion of the cochlea fluid instead of a hearing aid based on the type of conductive loss, amount of hearing loss and customer preference. Such prostheses include, for example, bone conduction devices and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem stimulators can also be proposed when a recipient experiences sensorineural hearing loss due to damage to the auditory nerve.

Some auditory prostheses use externally disposed microphone assemblies, while other auditory prostheses (e.g., "mostly implantable," "fully implantable," or "totally implantable" auditory prostheses) use subcutaneously implantable microphone assemblies or covered microphone assemblies. The subcutaneously implantable microphone assemblies are configured to be positioned (e.g., in a surgical procedure) beneath the skin and on, within, or proximate to the recipient's skull and at a location that facilitates the receipt of acoustic signals by the microphone assembly once implanted (e.g., at a location between the recipient's skin and skull, rearward and upward of the recipient's ear or in the mastoid region). Certain such auditory prostheses have the advantage of allowing the user to have a superior aesthetic result, as the recipient is visually indistinguishable in day-to-day activities from individuals that have not received such devices. Such devices also have a further advantage in generally being inherently waterproof, allowing the recipient to shower, swim, and so forth without needing to take any special measures. Examples of such devices include, but are not limited to, totally implanted cochlear implants ("TICIs"), mostly implantable cochlear implants ("MICI"), and fully implantable middle ear implants utilizing totally implantable acoustic ("TIA") systems.

The teachings detailed herein are applicable, in at least some embodiments, to any type of medical device utilizing a microphone assembly, including but not limited to auditory prostheses such as: electro-acoustic electrical/acoustic systems, cochlear implant devices, implantable hearing aid devices, middle ear implant devices, bone conduction devices (e.g., active bone conduction devices; passive bone conduction devices, percutaneous bone conduction devices; transcutaneous bone conduction devices), Direct Acoustic Cochlear Implant (DACI), middle ear transducer (MET), electro-acoustic implant devices, other electrically stimulating auditory prostheses (e.g., auditory brain stimulators), other types of auditory prosthesis devices, and/or combinations or variations thereof, or any other suitable hearing prosthesis system with or without one or more external components. Certain such embodiments can be referred to as "partially implantable," "semi-implantable," "mostly implantable," "fully implantable," or "totally implantable" auditory prostheses. In some embodiments, the teachings detailed herein and/or variations thereof can be utilized in other types of medical devices or prostheses beyond auditory prostheses that provide a wide range of therapeutic benefits to recipients, patients, or other users. For example, certain embodiments described herein can be used with other prostheses, sensors, pacemakers, drug delivery systems, defibrillators, functional electrical stimulation devices, catheters, etc. which utilize an acoustic sensor (e.g., a pressure transducer; a MEMS microphone).

In certain embodiments described herein, the medical device utilizes one or more implanted microphone assemblies on or within the recipient and/or one or more microphone assemblies that are positioned external to the recipient. For example, an external microphone assembly can be used to supplement an implantable microphone assembly. Thus, the teachings detailed herein and/or variations thereof can be utilized with any type of external or implantable microphone arrangement.

FIG. 1 is a perspective view of an example cochlear implant auditory prosthesis 100 implanted in a recipient in accordance with certain embodiments described herein. The example auditory prosthesis 100 is shown in FIG. 1 as comprising an implanted stimulator unit 120 (e.g., an actuator) and a microphone assembly 124 that is external to the recipient (e.g., a partially implantable cochlear implant). An example auditory prosthesis 100 (e.g., a totally implantable cochlear implant; a mostly implantable cochlear implant) in accordance with certain embodiments described herein can replace the external microphone assembly 124 shown in FIG. 1 with a subcutaneously implantable microphone assembly, as described more fully herein.

As shown in FIG. 1, the recipient has an outer ear 101, a middle ear 105, and an inner ear 107. In a fully functional ear, the outer ear 101 comprises an auricle 110 and an ear canal 102. An acoustic pressure or sound wave 103 is collected by the auricle 110 and is channeled into and through the ear canal 102. Disposed across the distal end of the ear canal 102 is a tympanic membrane 104 which vibrates in response to the sound wave 103. This vibration is coupled to oval window or fenestra ovalis 112 through three bones of middle ear 105, collectively referred to as the ossicles 106 and comprising the malleus 108, the incus 109, and the stapes 111. The bones 108, 109, and 111 of the middle ear 105 serve to filter and amplify the sound wave 103, causing the oval window 112 to articulate, or vibrate in response to vibration of the tympanic membrane 104. This vibration sets up waves of fluid motion of the perilymph within cochlea 140. Such fluid motion, in turn, activates tiny hair cells (not shown) inside the cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, the example auditory prosthesis 100 comprises one or more components which are temporarily or permanently implanted in the recipient. The example auditory prosthesis 100 is shown in FIG. 1 with an external component 142 which is directly or indirectly attached to the recipient's body, and an internal component 144 which is temporarily or permanently implanted in the recipient (e.g., positioned in a recess of the temporal bone adjacent auricle 110 of the recipient). The external component 142 typically comprises one or more sound input elements (e.g., an external microphone assembly 124 positioned by the recipient's auricle 110) for detecting sound, a sound processing unit 126 (e.g., disposed in a Behind-The-Ear unit), a power source (not shown), and an external transmitter unit 128.

During normal operation, ambient acoustic signals (e.g., ambient sound) are received by the microphone assembly 124 (e.g., for an implanted microphone assembly, the ambient acoustic signals impinge on the recipient's tissue and are received transcutaneously by the implanted microphone assembly). The signal processing unit 126 processes the output of the microphone assembly 124 to generate a processed audio drive signal (e.g., encoded signals, sometimes referred to herein as encoded data signals) which is provided to the external transmitter unit 128 (e.g., via a cable) and/or to other components of the auditory prosthesis. As will be appreciated, the sound processing unit 126 can utilize digital processing techniques to provide frequency shaping, amplification, compression, and other signal conditioning, including conditioning based on recipient-specific fitting parameters.

In the illustrative embodiments of FIG. 1, the external transmitter unit 128 comprises an external coil 130 (e.g., a wire antenna coil comprising multiple turns of electrically insulated single-strand or multi-strand platinum or gold wire) and, preferably, a magnet (not shown) secured directly or indirectly to the external coil 130. The external coil 130 of the external transmitter unit 128 is part of an inductive radio frequency (RF) communication link with the internal component 144.

The power source of the external component 142 is configured to provide power to the auditory prosthesis 100, where the auditory prosthesis 100 includes a battery (e.g., located in the internal component 144, or disposed in a separate implanted location) that is recharged by the power provided from the external component 142 (e.g., via a transcutaneous energy transfer link). The transcutaneous energy transfer link is used to transfer power and/or data to the internal component 144 of the auditory prosthesis 100. Various types of energy transfer, such as infrared (IR), electromagnetic, capacitive, and inductive transfer, may be used to transfer the power and/or data from the external component 142 to the internal component 144. During operation of the auditory prosthesis 100, the power stored by the rechargeable battery is distributed to the various other implanted components as needed.

The internal component 144 comprises an internal receiver unit 132, a stimulator unit 120, and an elongate electrode assembly 118. In some embodiments, the internal receiver unit 132 and the stimulator unit 120 are hermetically sealed within a biocompatible housing. The internal receiver unit 132 comprises an internal coil 136 (e.g., a wire antenna coil comprising multiple turns of electrically insulated single-strand or multi-strand platinum or gold wire), and preferably, a magnet (also not shown) fixed relative to the internal coil 136. The internal receiver unit 132 and the stimulator unit 120 are hermetically sealed within a biocompatible housing, sometimes collectively referred to as a stimulator/receiver unit. The internal coil 136 receives power and/or data signals from the external coil 130 via a transcutaneous energy transfer link (e.g., an inductive RF link). The stimulator unit 120 generates electrical stimulation signals based on the data signals, and the stimulation signals are delivered to the recipient via the elongate electrode assembly 118.

The elongate electrode assembly 118 has a proximal end connected to the stimulator unit 120, and a distal end implanted in the cochlea 140. The electrode assembly 118 extends from the stimulator unit 120 to the cochlea 140 through the mastoid bone 119. In some embodiments, the electrode assembly 118 may be implanted at least in the basal region 116, and sometimes further. For example, the electrode assembly 118 may extend towards apical end of cochlea 140, referred to as cochlea apex 134. In certain circumstances, the electrode assembly 118 may be inserted into the cochlea 140 via a cochleostomy 122. In other circumstances, a cochleostomy may be formed through the round window 121, the oval window 112, the promontory 123, or through an apical turn 147 of the cochlea 140.

The elongate electrode assembly 118 comprises a longitudinally aligned and distally extending array 146 of electrodes or contacts 148, sometimes referred to as electrode or contact array 146 herein, disposed along a length thereof. Although the electrode array 146 can be disposed on the electrode assembly 118, in most practical applications, the electrode array 146 is integrated into the electrode assembly 118 (e.g., the electrode array 146 is disposed in the electrode assembly 118). As noted, the stimulator unit 120 generates stimulation signals which are applied by the electrodes 148 to the cochlea 140, thereby stimulating the auditory nerve 114.

While FIG. 1 schematically illustrates an auditory prosthesis 100 utilizing an external component 142 comprising an external microphone assembly 124, an external sound processing unit 126, and an external power source, in certain other embodiments, one or more of the microphone assembly 124, sound processing unit 126, and power source are implantable on or within the recipient (e.g., within the internal component 144). For example, a totally or fully-implantable auditory prosthesis 100, such as a totally implantable cochlear implant ("TICI"), can have each of the microphone assembly 124, sound processing unit 126, and power source implantable on or within the recipient (e.g., encapsulated within a biocompatible assembly located subcutaneously on the recipient's skull). For another example, a mostly-implantable auditory prosthesis 100, such as a mostly-implantable cochlear implant ("MICI"), can have most of its components (e.g., excluding the microphone, which can be an in-the-ear-canal microphone) implantable on or within the recipient. The subcutaneously implantable microphone assembly 124 is configured to respond to auditory signals (e.g., sound; pressure variations in an audible frequency range) by generating output signals (e.g., electrical signals; optical signals; electromagnetic signals) indicative of the auditory signals received by the microphone assembly 124, and these output signals are used by the auditory prosthesis 100 to generate stimulation signals which are provided to the recipient's auditory system.

Figure 2:
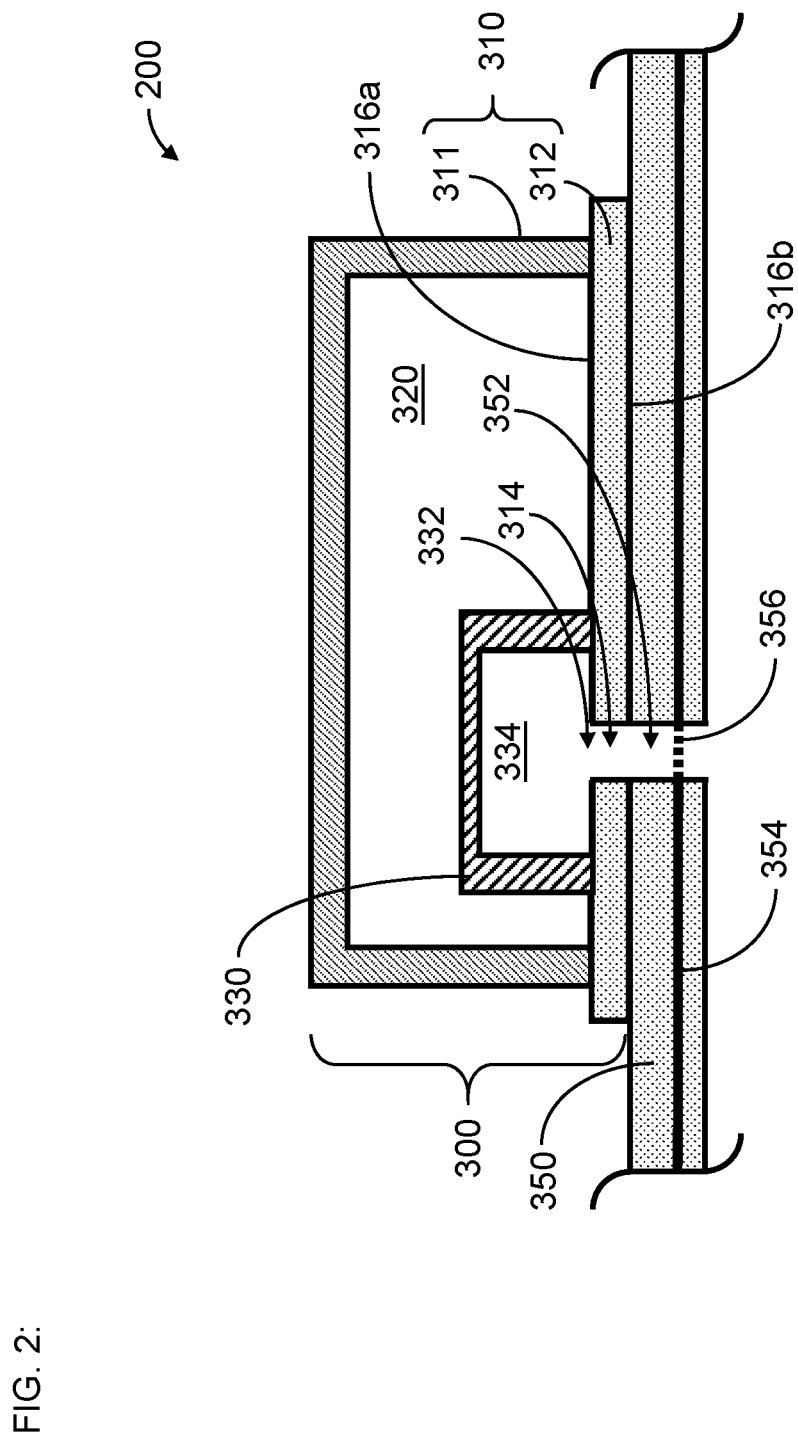
FIG. 2 schematically illustrates a cross-sectional view of an example assembly in accordance with certain embodiments described herein.

FIG. 2 schematically illustrates a cross-sectional view of an example assembly 200 in accordance with certain embodiments described herein. The assembly 200 comprises a package 300 and a printed circuit board (PCB) 350. The package 300 comprises a housing 310 bounding a region 320 and an acoustic sensor 330 (e.g., a pressure transducer; a microelectromechanical system (MEMS) microphone) within the region 320. The housing 310 comprising a base 312 with a first hole 314 (e.g., an acoustic port of the package 300), and the sensor 330 is configured to generate signals indicative of sound received by the sensor 330 through the first hole 314. The PCB 350 is in mechanical communication with the base 312 and the PCB 350 comprises a second hole 352 aligned with the first hole 314 such that sound received by the second hole 352 propagates through the first hole 314 to the sensor 330. The PCB 350 further comprises an electrically conductive layer 354. At least a portion 354 of the layer 356 extends across the second hole 352. The portion 354 is configured to allow the sound to propagate through the second hole 352 and is further configured to at least partially shield the region 320 containing the sensor 330 from electromagnetic interference.

Figure 3:
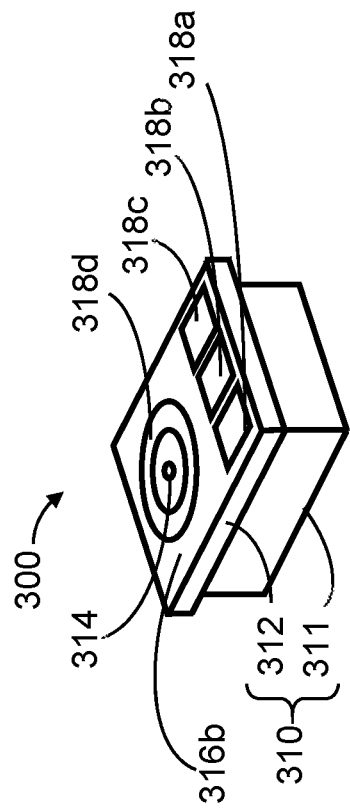
FIG. 3 schematically illustrates an example package in accordance with certain embodiments described herein.

FIG. 3 schematically illustrates an example package 300 in accordance with certain embodiments described herein. The example package 300 shown in FIG. 3 is a "bottom port MEMS microphone package" in which the first hole 314 extends through a surface of the base 312 configured to be mounted to the PCB 350 to the sensor 330 (e.g., MEMS microphone) within the region 320. The sensor 330 can comprise a pressure-sensitive diaphragm that is etched directly into a silicon wafer by MEMS processing techniques, and can further comprise an integrated preamplifier. As schematically illustrated in FIG. 2, the sensor 300 can comprise an acoustic port 332 and a front volume 334, and the first hole 314 can be aligned with an acoustic port 332 of the sensor 330. In certain embodiments, the package 300 has a volume of 10 mm$^2$ or less (e.g., dimensions of 4 mm×2.5 mm×1 mm or smaller), and is configured to be is surface-mountable (e.g., via a solder reflow process) onto the PCB 350. In certain embodiments, the package 300 has a small power consumption, low noise output, and is configured to have a flat and highly stable frequency response over time, temperature, and/or humidity. Examples of packages 300 in accordance with certain embodiments described herein are available from Sonion of Roskilde, Denmark, Knowles Electronics, LLC of Itasca, Illinois, STMicroelectronics N.V. of Geneva, Switzerland, Cirrus Logic, Inc. of Austin, Texas, and other microelectronics manufacturers.

In certain embodiments, the housing 310 comprises a lid 311 and the base 312, which is in mechanical communication with the lid 311 with the region 320 substantially surrounded by the lid 311 and the base 312. In certain embodiments, the lid 311 comprises a metal layer (e.g., Ni/Au, 304 stainless steel) that is in electrical communication with a ground layer of the base 312, with the lid 311 and the ground layer of the base 312 providing at least some electromagnetic interference (e.g., radio frequency or RF) shielding to the electronic components within the region 320.

In certain embodiments, the base 312 comprises a substrate having multiple electrically conductive layers (e.g., four layers comprising Cu and/or other metals) laminated with one or more electrically insulating layers (e.g., fiberglass; FR4) that separate the electrically conductive layers from one another. The base 312 comprises a first surface 316a comprising a plurality of first terminals (e.g., first solder pads of the electrically conductive layers of the base 312) in mechanical and electrical communication with (e.g., soldered to) one or more corresponding terminals (e.g., solder pads) of the sensor 330 mounted on the first surface 316a within the region 320 and to first circuitry (e.g., one or more other electronic components; at least one integrated circuit; processor; input buffer; differential output amplifier) mounted on the first surface 316a within the region 320 and in electrical communication with the sensor 330.

In certain embodiments, the base 312 further comprises a second surface 316b opposite to the first surface 316a, and the first hole 314 extends from the first surface 316a to the second surface 316b. The first hole 314 has a first perimeter at the first surface 316a and a second perimeter at the second surface 316b, which can be the same as or different from the first perimeter, and the first hole 314 can be circular or can have another shape (e.g., square; rectangular; slot-like).

The second surface 316b of certain embodiments further comprises a plurality of second terminals 318 (e.g., second solder pads of the electrically conductive layers of the base 312) configured to be in mechanical and electrical communication with corresponding third terminals (e.g., third solder pads) of the PCB 350. The example base 312 schematically illustrated by FIG. 3 comprises a land grid array (LGA) of four second terminals 318a, 318b, 318c, 318d, each of which is configured to be soldered to a corresponding third terminal on a surface of the PCB 350. For example, a pair of second terminals 318a, 318b can be configured to provide differential output signals (e.g., inverted output signals and non-inverted output signals, respectively) from the package 300 to the PCB 350, another second terminal 318c can be configured to provide electrical power from the PCB 350 to the package 300, and still another second terminal 318d can encircle the first hole 314 and can be at ground (e.g., in electrical communication with a ground layer of the base 312). In certain other embodiments, the number of second terminals 318 can depend on whether the sensor 330 (e.g., MEMS microphone) is digital or analog.

Figure 4:
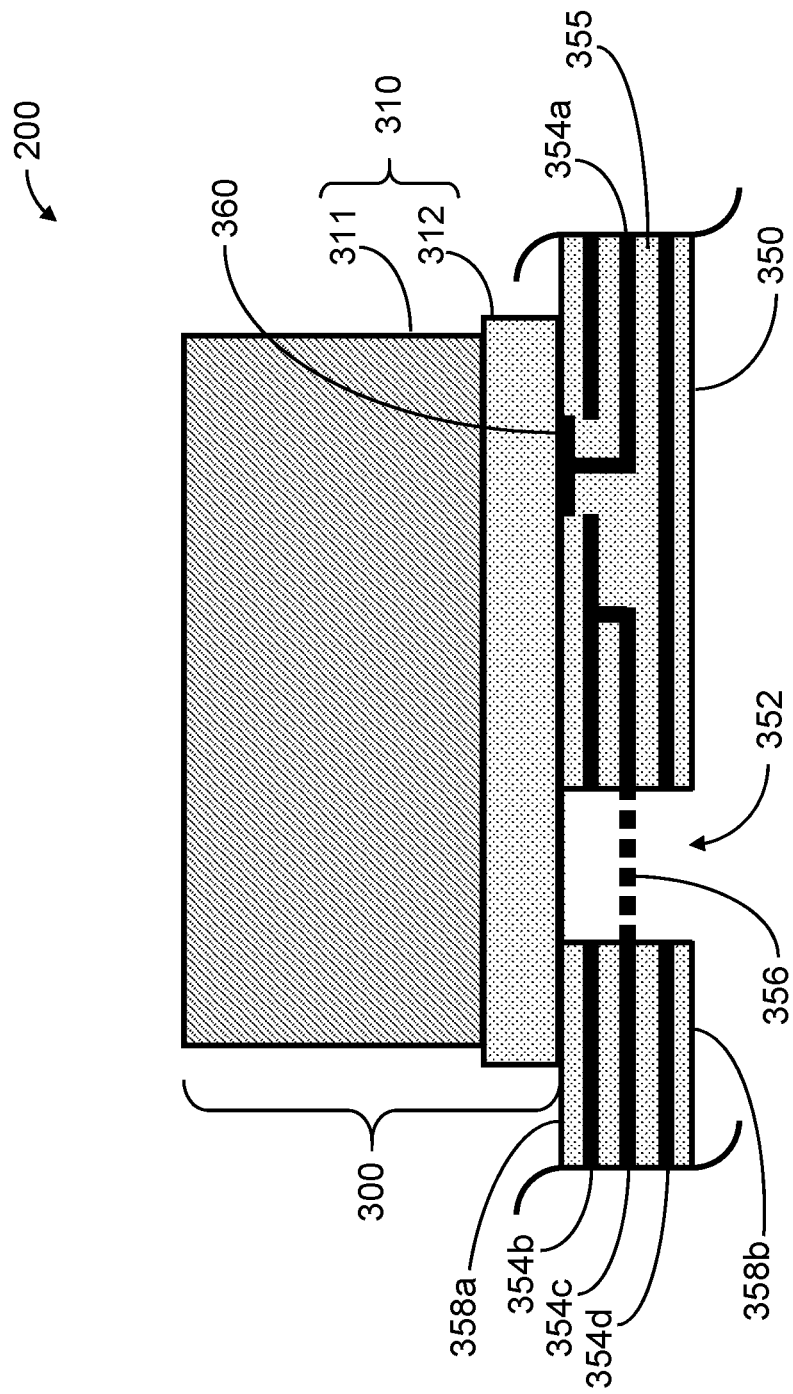
FIG. 4 schematically illustrates an example PCB with a package mounted thereon in accordance with certain embodiments described herein.

FIG. 4 schematically illustrates an example PCB 350 with an example package 300 mounted thereon in accordance with certain embodiments described herein. FIG. 4 shows a cross-sectional view of the example PCB 350 and a side view of the example package 300. In certain embodiments, the PCB 350 further comprises a plurality of electrically conductive layers 354 (e.g., comprising Cu and/or other metals) laminated with one or more electrically insulating layers 355 (e.g., fiberglass; FR4) that separate the electrically conductive layers 354 from one another. For example, at least one electrically conductive layer 354 can be a ground plane (e.g., configured to provide a ground voltage to the package 300), at least one electrically conductive layer 354 can be a signal plane (e.g., configured to receive a signal from the package 300), and at least one electrically conductive layer 354 can be a power plane (e.g., configured to provide power to the package 300). In certain embodiments, the PCB 350 is structurally rigid, while in certain other embodiments, the PCB 350 is structurally flexible.

In certain embodiments, the PCB 350 comprises a third surface 358a and a fourth surface 358b opposite to the third surface 358a, and the second hole 352 of the PCB 350 extends from the third surface 358a to the fourth surface 358b. The package 300 is mounted on the third surface 358a of the PCB 350. The second hole 352 can have a third perimeter at the third surface 358a and a fourth perimeter at the fourth surface 358b which is the same as or is different from the third perimeter. The second hole 352 is aligned with the first hole 314 such that sound received by the second hole 352 propagates through the second hole 352 and through the first hole 314 to the sensor 330 (e.g., the first hole 314, the second hole 352, and the acoustic port 332 of the sensor 330 are in fluidic communication with one another). For example, each of the first hole 314 and the second hole 352 can have a corresponding central axis, with the central axes aligned with one another or displaced from one another while allowing acoustic pressure waves to propagate through the second hole 352 and through the first hole 314 to the sensor 330. In certain embodiments, the third perimeter of the second hole 352 is larger than the second perimeter of the first hole 314.

In certain embodiments, the third surface 358a of the PCB 350 has a plurality of third terminals 360 (e.g., third solder pads of the electrically conductive layers 354) in mechanical and electrical communication with (e.g., soldered to) one or more corresponding second terminals 318 (e.g., second solder pads) of the package 300. For example, as shown in FIG. 4, the example PCB 350 comprises at least one electrically conductive layer 354a in electrical communication with at least one corresponding terminal 360 which is in electrical communication with a corresponding terminal of the package 300, and the at least one layer 354a and the at least one terminal 360 are configured to receive output signals from the package 300 (e.g., electrical signals indicative of sound received by the package 300) and to provide the output signals to other circuitry (e.g., signal processing circuitry). At least some of the other electrically conductive layers 354b,c,d are configured to be connected to ground voltage and to provide at least some electromagnetic interference (e.g., radio frequency or RF) shielding to the layer 354a (e.g., by having at least a portion of the layer 354a between two of the layers 354b,d). In certain embodiments, at least one electrically conductive layer 354 and at least one corresponding terminal 360 are configured to provide electrical power to at least one corresponding second terminal 318 of the package 300, and at least one other electrically conductive layer 354 and at least one corresponding terminal 360 are configured to provide a ground voltage to at least one corresponding second terminal 318 of the package 300.

In certain embodiments, as schematically illustrated by FIG. 4, at least a portion 356 of at least one electrically conductive layer 354 (e.g., layer 354c) of the PCB 350 extends across the second hole 352. In certain embodiments, the portion 356 of the electrically conductive layer 354 is in electrical communication with a ground voltage (e.g., the layer 354c is a ground plane of the PCB 350), while in certain other embodiments, the portion 356 is in electrical communication with a power plane or an amplified signal plane of the PCB 350. In certain embodiments, the portion 356 is configured to provide at least some electromagnetic interference (e.g., radio frequency or RF) shielding to the package 300 (e.g., by reducing the amount of electromagnetic interference that would otherwise reach the sensor 330 through the first hole 314 and the second hole 352). For example, the portion 356 of the electrically conductive layer 354 can comprise a mesh (e.g., grid; lattice; 90 degree hatched polygonal pattern) of an electrically conductive material (e.g., Cu) that is electrically grounded, is free-hanging within the second hole 352, and has a plurality of apertures (e.g., orifices) through which sound can propagate.

In certain embodiments, the portion 356 allows air to pass through the portion 356 while providing an electrostatic shield (e.g., like a Faraday cage). While FIG. 4 shows the portion 356 being part of the electrically conductive layer 354c, which is between two other electrically conductive layers 354b,d (e.g., of a three-layered PCB 350), in certain other embodiments, the portion 356 is part of other electrically conductive layers 354 of the PCB 350.

In certain embodiments, the portion 356 is configured to protect against particulates (e.g., dust; droplets) from entering the acoustic port 332 of the sensor 330 and/or to protect against electromagnetic interference (EMI) and/or electrostatic discharge (ESD) from damaging or otherwise adversely affecting the performance of the sensor 330 or other circuitry within the package 300. For example, the portion 356 can comprise a hydrophobic coating configured to make the portion 356 resistant to penetration of liquid water.

In certain embodiments, the portion 356 is configured to provide a predetermined shielding effectiveness to mitigate (e.g., prevent; block) EMI and/or ESD from damaging or otherwise adversely affecting the performance of the package 300. For example, the portion 356 can comprise a mesh having a hatched polygonal pattern with an aperture size (D), thickness (L), and number of apertures (K). The dimensions of the mesh can be configured based on the frequency ($f=c/\lambda$, where f is the frequency, c is the speed of light, and $\lambda$ is the wavelength) of the electromagnetic interference to be shielded. Maximum shielding effectiveness would be provided by a solid portion 356 having no apertures, but this configuration would block the acoustic performance of the assembly 200.

In certain embodiments, the portion 356 is configured to alter the acoustic impedance of the second hole 352 that, along with the acoustic performance of the package 300, influences the acoustic performance (e.g., the acoustic frequency response) of the assembly 200. For example, the aperture size (D) and the number of apertures (K) can be selected to provide a predetermined acoustic frequency response. The first hole 314, the second hole 352, and the front volume 334 of the sensor 330 form a second-order low-pass filter of acoustic signals. In certain embodiments, the thickness of the portion 356 and the radius of the apertures of the portion 356 are configured to provide a predetermined acoustic resistance and/or a predetermined acoustic frequency response.

In certain embodiments, the assembly 200 further comprises second circuitry mounted on the PCB 350, the second circuitry in electrical communication with the package 300. For example, the second circuitry can comprise signal processing circuitry having one or more other electronic components (e.g., at least one integrated circuit; processor; input buffer; differential output amplifier). In certain embodiments, at least some of the second circuitry is mounted onto the third surface 358a of the PCB 350 (e.g., the same surface on which the package 300 is mounted onto the PCB 350) and/or onto the fourth surface 358b of the PCB 350 (e.g., the surface opposite to the surface on which the package 300 is mounted onto the PCB 350).

Figure 5:
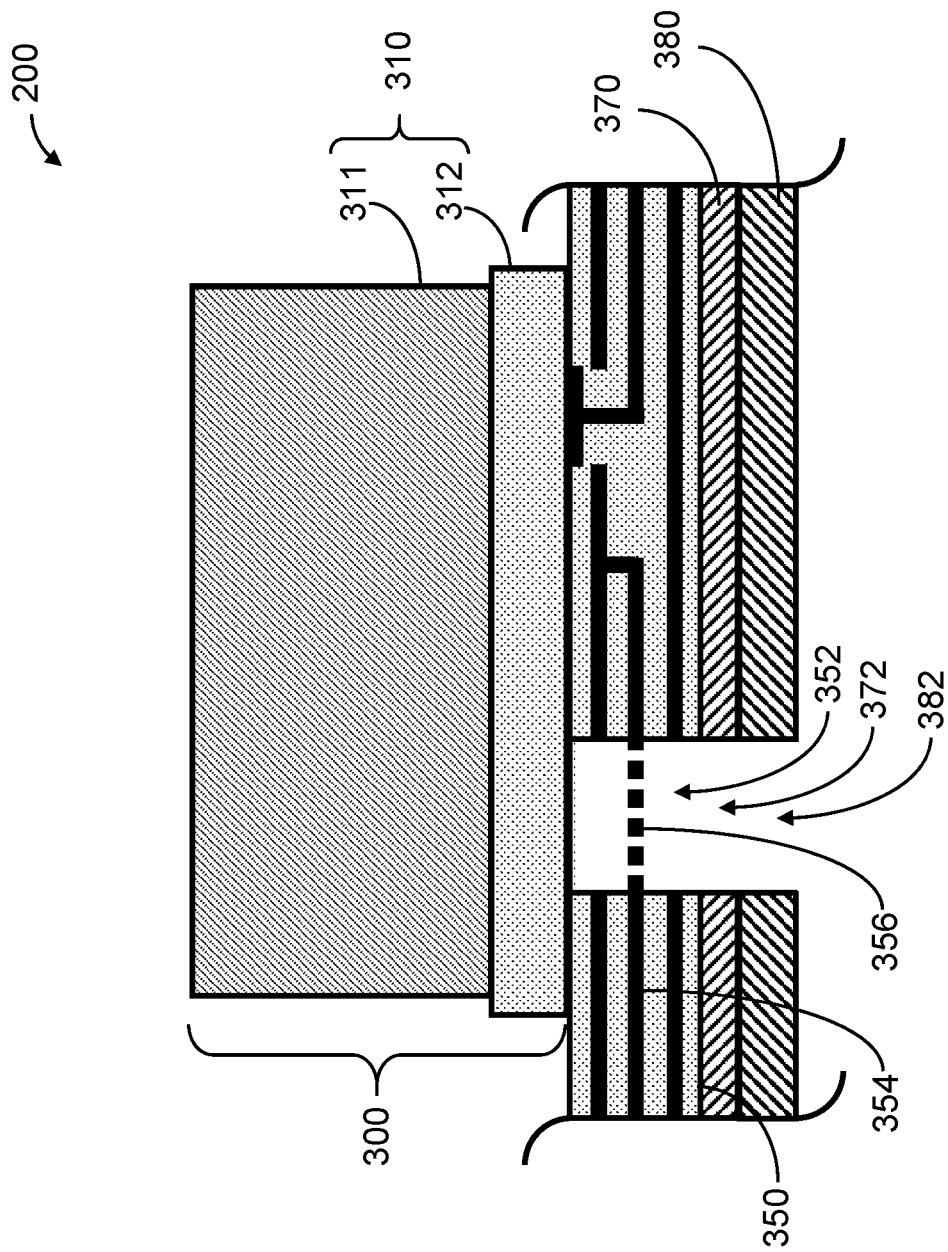
FIG. 5 schematically illustrates an example assembly comprising at least one gasket and at least one casing in accordance with certain embodiments described herein.

FIG. 5 schematically illustrates an example assembly 200 comprising at least one gasket 370 (e.g., rubber; elastomer) and at least one casing 380 in accordance with certain embodiments described herein. For example, the at least one casing 380 can comprise a biocompatible material (e.g., titanium) and can be configured to be implantable on or within a recipient. In certain embodiments, the gasket 370 is sandwiched between the PCB 350 and the casing 380 and is configured to provide a sufficiently tight mechanical seal around the second hole 352 (e.g., to reduce or block unwanted acoustic noise or acoustic coupling from other components of the system). In certain embodiments, the casing 380 is biocompatible and contains the package 300, the PCB 350, and the gasket 370 such that the assembly 200 is configured to be implanted within the body of a recipient.

As schematically illustrated by FIG. 5, in certain embodiments, the gasket 370 comprises a third hole 372 and the casing 380 comprises a fourth hole 382, with the fourth hole 382 and the third hole 372 in fluidic communication (e.g., aligned) with one another and with the second hole 352, the first hole 314, and the acoustic port 332 of the sensor 330 (e.g., such that sound received by the fourth hole 382 propagates through the fourth hole 382, the third hole 372, the second hole 352, the portion 356, the first hole 314, and the acoustic port 332). In certain embodiments, the dimensions (e.g., shape, length, and perimeter) of the third hole 372 and the fourth hole 382 affect the acoustic frequency response of the assembly 200, the effects of which can be calculated using the equations disclosed herein and used to tailor the acoustic frequency response of the assembly 200. In certain embodiments, the third hole 372 and the fourth hole 382 have larger perimeters than do the second hole 352 and the first hole 314.

Figure 6:
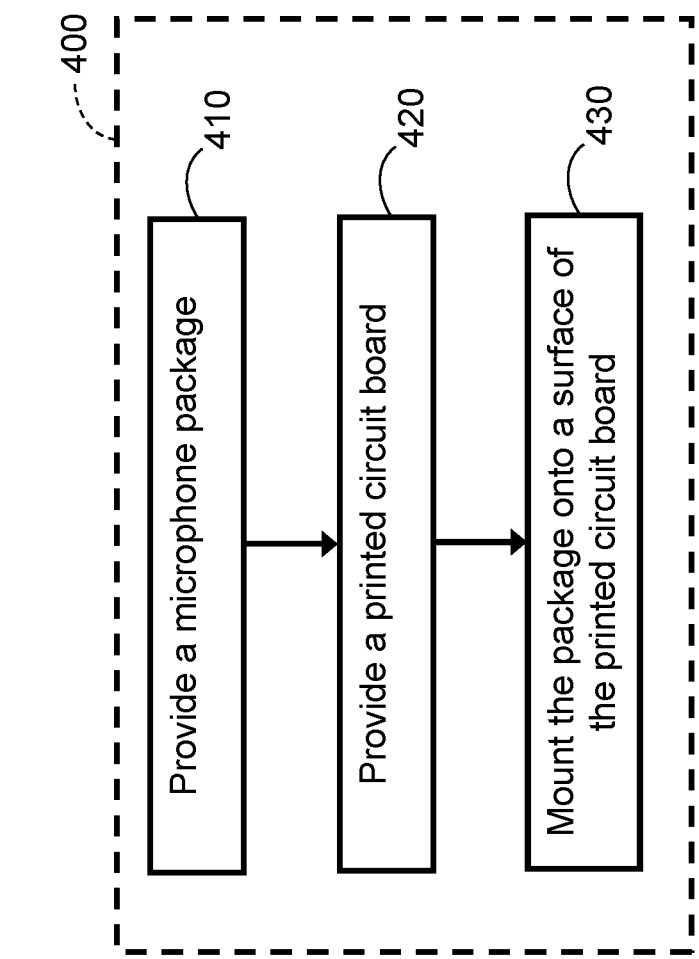
FIG. 6 is a flow diagram of an example method in accordance with certain embodiments described herein.

FIG. 6 is a flow diagram of an example method 400 in accordance with certain embodiments described herein. In an operational block 410, the method 400 comprises providing a microphone package (e.g., package 300 comprising an acoustic sensor 330) comprising an acoustic port (e.g., first hole 314), the package configured to be surface-mounted onto a printed circuit board (e.g., PCB 350) and configured to generate signals indicative of sound received by the acoustic port. In an operational block 420, the method 400 further comprises providing the printed circuit board, the printed circuit board comprising a hole (e.g., second hole 352) and an electrically conductive layer (e.g., portion 356 of electrically conductive layer 354) extending across the hole. In an operational block 430, the method 400 further comprises mounting the package onto a surface (e.g., the third surface 358a of PCB 350) of the printed circuit board such that sound received by the hole propagates to the acoustic port.

In certain embodiments, mounting the package onto the surface of the printed circuit board comprises aligning the acoustic port with the hole. For example, the acoustic port of the package can be aligned with the hole of the printed circuit board such that sound received by the hole propagates through the acoustic port to a microphone within the package (e.g., the acoustic port of the package and the hole of the printed circuit board are in fluidic communication with one another). In certain embodiments, mounting the package further comprises soldering electrically conductive pads of the package (e.g., second terminals 318 of the package 300) to electrically conductive second pads of the printed circuit board (e.g., third terminals 360 of the PCB 350). In certain embodiments, the package further comprises a sensor 300 having a sensor acoustic port (e.g., acoustic port 332) which is aligned with the acoustic port of the package such that sound received by the acoustic port of the package propagates through the sensor acoustic port.

In certain embodiments, the electrically conductive layer of the printed circuit board is configured to mitigate (e.g., prevent; block) electromagnetic interference and/or electrostatic discharge from damaging a sensor within the package or otherwise adversely affecting performance of the package. For example, the electrically conductive layer of the printed circuit board can be in electrical communication with a voltage source (e.g., ground) and can extend fully across the hole of the printed circuit board. In certain embodiments, the electrically conductive layer of the printed circuit board is configured to protect against particulates (e.g., dust; droplets) from entering the acoustic port of the package (e.g., the electrically conductive layer comprises a hydrophobic coating).

In certain embodiments, the electrically conductive layer of the printed circuit board is configured to allow sound to propagate through the electrically conductive layer (e.g., the electrically conductive layer comprises a plurality of apertures through which sound can propagate). In certain such embodiments, the hole and the electrically conductive layer are configured to have a predetermined acoustic impedance. For example, the hole can have a predetermined length, shape, and cross-sectional area (e.g., circular with a predetermined radius) and the portion of the electrically conductive layer within the hole can comprise a mesh having a hatched polygonal pattern with a predetermined aperture size, thickness, and number of apertures.

In certain embodiments, the method 400 further comprises, after mounting the package onto the surface of the printed circuit board, placing the package and the printed circuit board within a biocompatible casing configured to be implanted in a recipient. For example, the package and the printed circuit board can be placed within a biocompatible casing 380 with a gasket 370 sandwiched between the printed circuit board and the casing. The casing can comprise a hole (e.g., fourth hole 382), the gasket can comprise a hole (e.g., third hole 372), and these holes can be aligned with the hole (e.g., second hole 352) of the printed circuit board and the acoustic port (e.g., first hole 314) such that sound received by the hole of the casing propagates through the other holes and the acoustic port to a microphone within the package (e.g., the acoustic port of the package and the holes of the printed circuit board, gasket, and casing are in fluidic communication with one another).

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. An assembly comprising:
   a package comprising a housing bounding a region and an acoustic sensor within the region, the housing comprising a base with a first hole, the sensor configured to generate signals indicative of sound received by the sensor through the first hole; and
   a printed circuit board in mechanical communication with the base, the printed circuit board comprising:
   a second hole aligned with the first hole such that sound received by the second hole propagates through the first hole to the sensor; and
   an electrically conductive layer, at least a portion of the layer extending across the second hole, the portion configured to allow the sound to propagate through the second hole and to at least partially shield the region containing the sensor from electromagnetic interference.

2. The assembly of claim 1, wherein the sensor comprises a microelectromechanical system (MEMS) microphone.

3. The assembly of claim 1, wherein the base comprises:
a first surface and a second surface opposite to the first surface, the first hole extending from the first surface to the second surface; and
first circuitry in electrical communication with the sensor, the sensor mounted on the first surface within the region.

4. The assembly of claim 3, wherein the first circuitry comprises at least one integrated circuit mounted on the first surface within the region and in electrical communication with the sensor.

5. The assembly of claim 3, wherein the printed circuit board comprises a third surface and a fourth surface opposite to the third surface, the second hole extending from the third surface to the fourth surface.

6. The assembly of claim 5, wherein the first surface of the base comprises a plurality of electrically conductive first pads and the second surface of the base comprises a plurality of electrically conductive second pads, the sensor in electrical communication with the first pads, the printed circuit board comprising a plurality of electrically conductive third pads on the third surface, at least some of the third pads in electrical communication with the second pads of the base.

7. The apparatus of claim 1, wherein the electrically conductive layer comprises a mesh.

8. The apparatus of claim 1, wherein the electrically conductive layer is in electrical communication with an electrical ground.

9. The assembly of claim 1, further comprising second circuitry mounted on the printed circuit board, the second circuitry in electrical communication with the package.

10. The assembly of claim 1, further comprising:
a biocompatible casing containing the package and the printed circuit board; and
a gasket sandwiched between a portion of the casing and the printed circuit board, the gasket comprising a third hole and the portion of the casing comprising a fourth hole, the third hole and the fourth hole aligned with the first hole and the second hole such that sound received by the fourth hole propagates through the fourth, third, second, and first holes to the sensor.

11. A method comprising:
providing a microphone package comprising an acoustic port, the package configured to be surface-mounted onto a printed circuit board and configured to generate signals indicative of sound received by the acoustic port;
providing the printed circuit board, the printed circuit board comprising a hole and an electrically conductive layer extending across the hole; and
mounting the package onto a surface of the printed circuit board such that sound received by the hole propagates to the acoustic port.

12. The method of claim 11, wherein said mounting comprises aligning the acoustic port with the hole.

13. The method of claim 12, wherein said mounting further comprises soldering electrically conductive pads of the package to electrically conductive pads of the printed circuit board.

14. The method of claim 11, wherein the electrically conductive layer is configured to mitigate electromagnetic interference and/or electrostatic discharge from damaging a sensor within the package or otherwise adversely affecting performance of the package.

15. The method of claim 11, wherein the hole and the electrically conductive layer are configured to have a predetermined acoustic impedance.

16. The method of claim 11, further comprising, after mounting the package onto the surface of the printed circuit board, placing the package and the printed circuit board within a biocompatible casing configured to be implanted in a recipient.

17. The assembly of claim 1, wherein
the sensor comprises a microphone comprising a pressure transducer and having a first frequency response to pressure waves, the electrically conductive layer comprising
an electrically conductive mesh within the second hole, the second hole and the mesh configured to alter an acoustic impedance of the second hole such that the assembly has a second frequency response to pressure waves different from the first frequency response.

18. The assembly of claim 17, wherein the microphone is surface-mountable and the pressure transducer is a microelectromechanical system (MEMS) pressure transducer.

19. The assembly of claim 17, wherein the microphone further comprises an acoustic port in fluidic communication with the pressure transducer and with the second hole of the printed circuit board.

20. The assembly of claim 17, wherein the microphone further comprises a plurality of first terminals and the printed circuit board further comprises a plurality of second terminals mounted to the plurality of first terminals.

21. The assembly of claim 20, wherein the plurality of first terminals is on a planar outer surface of the microphone.

22. The assembly of claim 20, wherein the microphone comprises a plurality of electrically conductive first layers in electrical communication with the plurality of first terminals.

23. The assembly of claim 22, wherein the printed circuit board comprises a plurality of electrically conductive second layers in electrical communication with the plurality of second terminals.

24. The assembly of claim 17, wherein the mesh is configured to at least partially shield the pressure transducer from electromagnetic interference (EMI) and/or electrostatic discharge (ESD).

25. The assembly of claim 24, wherein the second hole and the mesh are configured to have a predetermined acoustic impedance.

26. The assembly of claim 24, wherein the mesh has a hatched polygonal pattern with an aperture size, thickness, and number of apertures.

27. The assembly of claim 26, wherein the mesh is configured to have a predetermined shielding effectiveness for mitigating EMI and/or ESD from damaging or otherwise adversely affecting performance of the assembly.

* * * * *